United States Patent
Steiner

(10) Patent No.: US 8,183,022 B2
(45) Date of Patent: May 22, 2012

(54) USE OF ETHANOL PLANT BY-PRODUCTS FOR YEAST PROPAGATION

(75) Inventor: Gadi Steiner, Champaign, IL (US)

(73) Assignee: Archer Daniels Midland Company, Decatur, IL (US)

( * ) Notice: Subject to any disclaimer, the term of this patent is extended or adjusted under 35 U.S.C. 154(b) by 590 days.

(21) Appl. No.: 12/262,315

(22) Filed: Oct. 31, 2008

(65) Prior Publication Data

US 2009/0117632 A1     May 7, 2009

Related U.S. Application Data

(60) Provisional application No. 61/001,714, filed on Nov. 2, 2007.

(51) Int. Cl.
*C12P 7/06*     (2006.01)

(52) U.S. Cl. ........................................ 435/161

(58) Field of Classification Search .................. 435/161
See application file for complete search history.

(56) References Cited

U.S. PATENT DOCUMENTS

2007/0184541 A1    8/2007    Karl et al.

OTHER PUBLICATIONS

International Search Report dated Jan. 29, 2009.
Forest Product Laboratory, Forest Service U.S. Department of Agriculture, "Food-Yeast Production from Wood-Processing by Products", U.S. Forest Service Research Note, FPL-065, Nov. 1964.

*Primary Examiner* — Karen Carlson
(74) *Attorney, Agent, or Firm* — Mark W. Roberts

(57) ABSTRACT

Embodiments of the invention relate, for example, to methods for reducing the load of organic acids and glycerol in water recycled to the fermentation process. Organic acids and glycerol produced during ethanol fermentation are used as a replacement for carbohydrates for propagation of yeast. The yeast may be sold as a feed product or used in subsequent fermentation.

15 Claims, 7 Drawing Sheets

USE OF ETHANOL PLANT BY-PRODUCTS FOR YEAST PROPAGATION

CROSS-REFERENCE TO RELATED APPLICATION

This application claims the benefit of U.S. Patent Application Ser. No. 61/001,714 filed Nov. 2, 2007, U.S. Patent Application Ser. No. 61/001,714 is incorporated by reference as if fully rewritten herein.

STATEMENT OF FEDERALLY SPONSORED RE-SEARCH

None.

BACKGROUND OF THE INVENTION

The following includes information that may be useful in understanding the present teachings. It is not an admission that any of the information provided herein is prior art, or material, to the presently described or claimed subject matter, or that any publication or document that is specifically or implicitly referenced is prior art.

FIELD OF THE INVENTION

The present teachings relate to, but are not limited to, the fields of ethanol fermentation, yeast production, and decreasing waste volume from those processes. Embodiments relate, for example, to methods for reducing the load of organic acids (acetic acid and lactic acid) and glycerol in water recycled to the fermentation process. Embodiments also relate, for example, to use of ethanol fermentation by-products as feedstock for yeast production. Methods of fermenting yeast and of preparing a yeast innocutla are also provided.

BACKGROUND OF THE ART

FIG. 1 illustrates a typical process for managing the incoming media, inoculum, product, and byproduct streams in an ethanol fermentation plant. In anaerobic fermentor 10 ethanol is made by anaerobic fermentation of yeast (usually a strain of *Saccharomyces cerevisiae*) in media containing as a primary carbon source, dextrose (or other sugar or polysaccharide of C5 or greater). Prior to fermentation, the yeast may be propagated by the inoculation train, in which the inoculum is grown in a succession of aerated fermentors of increased volume. The composition of those fermentors is water from different possible sources, as well as corn mash and enzymes.

After the ethanol fermentation is completed, the liquid stream is fed to a still 30, where ethanol is separated from the stream. Biomass and other particulate matter from the fermentation are then separated from the fermentation liquid by gravity, centrifugation, or filtration in a separator 20. The dried, separated solids containing the biomass are concentrated, eventually dried, and are commonly referred to as distillers dried grains (DDGs). DDGs are typically sold as animal feed or animal feed components.

The remainder of the aqueous phase solution from the fermentation media is commonly referred to as "backset." The principle carbon compounds in the backset are dilute organic acids and glycerol ("OAG"). A portion of the backset (typically about 35%) is recovered and returned to the original anaerobic fermentor 10 to supplement the amount of water (either fresh water or process water) that must be used during fermentation. Organic acids and glycerol can not be used by yeast as a carbon source during anaerobic fermentation; these compounds are actually formed from dextrose by yeasts and contaminating organisms. Continuous recycling of backset into the anaerobic fermentor 10 can result in a build up of organic acids and glycerol that would inhibit ethanol production. Therefore, in a continuous process, most of the backset is directed away to waste water or to an evaporation system, as shown in "Other Treatment Steps" in FIG. 1.

The evaporation system, within "Other Treatment Steps," recovers a portion of the water from the backset, which is combined with the primary backset flow and other water sources to be sent to the anaerobic fermentor. The remainder of the aqueous phase is therefore a concentrated solution of OAG, which may be used as animal feed, for example, by being combined with DDGs and dried. The OAG may also need to be disposed of as a waste product. Usually the OAG is a "negative value" product that does not increase the financial yield of a fermentation.

BRIEF SUMMARY OF THE INVENTION

Organic acids and glycerol are two by-products formed during anaerobic fermentation of yeast to product ethanol. I have found that these by-products of an anaerobic fermentation are useful substrates for yeasts in aerobic fermentation. This has a number of beneficial consequences. For example, it allows the carbon contained within the organic acids and glycerol to be used as a carbon source for the aerobic growth of yeast. This aerobically grown yeast may, in turn, be used as an inoculum for anaerobic fermentation.

Embodiments of the invention provide, for example, methods of recycling OAG produced during ethanolic fermentation of yeast on dextrose or other sugars. One embodiment provides a method for making ethanol by a batch fermentation, comprising growing an ethanol producing microorganism under first growth conditions in a first medium comprising a carbon source. That carbon source comprises at least one organic acid (for example, acetic acid, lactic acid, or both) and glycerol, which are obtained as a by-product of growing the microorganism in a second medium to produce ethanol by fermentation. The second medium comprises a carbon source such as a sugar or a saccharide of at least 5 carbon atoms; the microorganism is grown m in the second medium, producing ethanol and said by-product. In a typical embodiment, the ethanol producing microorganism is *Saccharomyces cerevisiae*, and the first medium carbon source consists essentially of water, micronutrients, and as carbon source acetic acid, lactic acid, and glycerol, and said second medium consists essentially of water, nutrients, and as carbon source dextrose. In another embodiment, the first medium comprises as carbon source acetic acid, lactic acid, and glycerol, and the second medium comprises dextrose as carbon source.

Those skilled in the art will recognize that media of the invention will include other nutrients that are necessary for the growth of the microorganism. Microbial propagation media usually contain, in addition to at least one carbon source, at least one nitrogen source. Typical nitrogen sources are, for example, ammonia, ammonium salt, amino acids, nitrates, or nitrites. In addition to nitrogen, other minerals are typically included. These include, for example, potassium, magnesium, sodium, sulfur, and phosphorus, which are usually included in concentrations between 0.05 to 2 g/l. Other trace elements are included at a concentration level of milligrams per liter, for example, between 1 and 5 mg/L. Those elements can include, for example, iron in the ferric and/or ferrous forms, molybdenum, cobalt, calcium, zinc, manganese, iodine, copper, and boron. Trace elements are usually found in the medium in their ionic forms.

Other nutrients that may be found in the medium include vitamins, including B-vitamin-complex vitamins. Precursors of nucleic acids may also be found and utilized in the medium. In production media like the ones used reported herein, the required components are typically found in excess of requirements. It is still possible that supplementation of some of those components might be required in some applications.

A further embodiment includes method for making ethanol by fermentation, comprising growing an ethanol producing microorganism under aerobic conditions in a first medium including a carbon source comprising organic acid and/or glycerol to form an inoculation broth. The inoculation broth is combined with a second medium comprising a carbon source including a sugar and/or a saccharide of at least 5 carbon atoms. The microorganism is grown under anaerobic conditions to produce ethanol and a byproduct comprising at least one member of the group consisting of organic acid and glycerol. The source of the byproducts can also be contaminating organisms that are typically present in ethanol fermentations.

In a typical embodiment, the microorganism is *Saccharomyces cerevisiae*, said first medium consists essentially of nutrients, and as carbon source lactic acid, acetic acid, glycerol, and water, and said second medium consists essentially of nutrients, and as carbon source dextrose and water. In a further embodiment, the first medium comprises as carbon source lactic acid, acetic acid, and glycerol, and the second medium comprises as carbon source dextrose. In some embodiments other nutrients required for growth are found in adequate amounts in the recycled liquid fractions that contain the OAGs. In some embodiments, nitrogen may need to be supplemented for growth, and in further embodiments nitrogen and other nutrients not present in adequate amounts in the recycled water streams some nutrients may also need to be supplemented.

A still further embodiment includes a method for making a primary product by fermentation, comprising growing a microorganism in continuous culture that produces the inoculum for the fermentation under a second condition, under first fermentation conditions in a first medium comprising a by-product of fermentation of the same microorganism culture under second conditions selected to produce the primary product; growing the microorganism culture under the second fermentation conditions in a second medium to produce the primary product and a by-product containing the primary nutrient source from step 1; separating the by-product containing the primary nutrient source from the primary product and the second medium to obtain a by-product stream; and providing the by-product stream to grow the microorganism aerobically in continuous culture.

In a further embodiment, methods described herein include the further step of concentrating the by-product stream prior to growing the microorganism in the first medium. Greater concentration of the by-product stream yields a higher resulting biomass. Fermentation conditions for embodiments of the invention may be aerobic. If OAGs are used as a substrate, the fermentation will be aerobic.

The culture growing in the first medium can be propagated both as a batch culture and as a continuous culture. When culture is grown in a continuous mode, this provides the ability to utilize fermentor volumes that are much smaller than currently used produce inoculum for the second stage. This provides a better utilization of the fermentor and auxiliary system. Using the continuous fermentation also enables more use of the fermentors growing the inoculum than is currently attained in the industry. Utilization is up to sixteen times the utilization of previous processes.

Current methods of inoculum propagation are dependent on two processes: the enzymatic breakdown of starch or other carbon source to produce sugars that can be utilized by the culture and the growth of the culture is dependent at the rate that the starch degrades. Methods provided herein have a readily available substrate in easily quantifiable amounts. Repeatability and consistency of the inoculum tend to be better than those of prior art methods.

In experiments that have been performed using some or all of the teachings herein, yeast yield of at least about $1 \times 10^8$ yeast cells/ml of media for every 1 g/l of OAGs consumed was achieved. Yeast concentrations of $1.5 \times 10^9$ cells/ml and growth rates in continuous culture of $3 \times 10^8$ g/l/hour to $4 \times 10^8$ g/l/hour were achieved.

Typically, fermentations are conducted using a strain of yeast, typically a strain of the genus *Saccharomyces*, and more typically a strain of *Saccharomyces cerevisiae*. The microorganism may also be, for example, a strain of *Corynebacterium*, a strain of *Staphylococcus*, or a strain of *Listeria*

DETAILED DESCRIPTION OF THE INVENTION

The present teaching describes several different features and aspects of the invention with reference to various exemplary embodiments. It is understood, however, that the invention embraces numerous alternative embodiments, which may be accomplished by combining any of the different features and aspects described herein in any combination that one of ordinary skill in the art would find useful.

Processing methods and products as described herein may offer many advantages over the prior art. Of course, the scope of the invention is defined by the claims, and whether an embodiment is within that scope should not be limited by whether the method provides one or more of these advantages.

Figure 1:
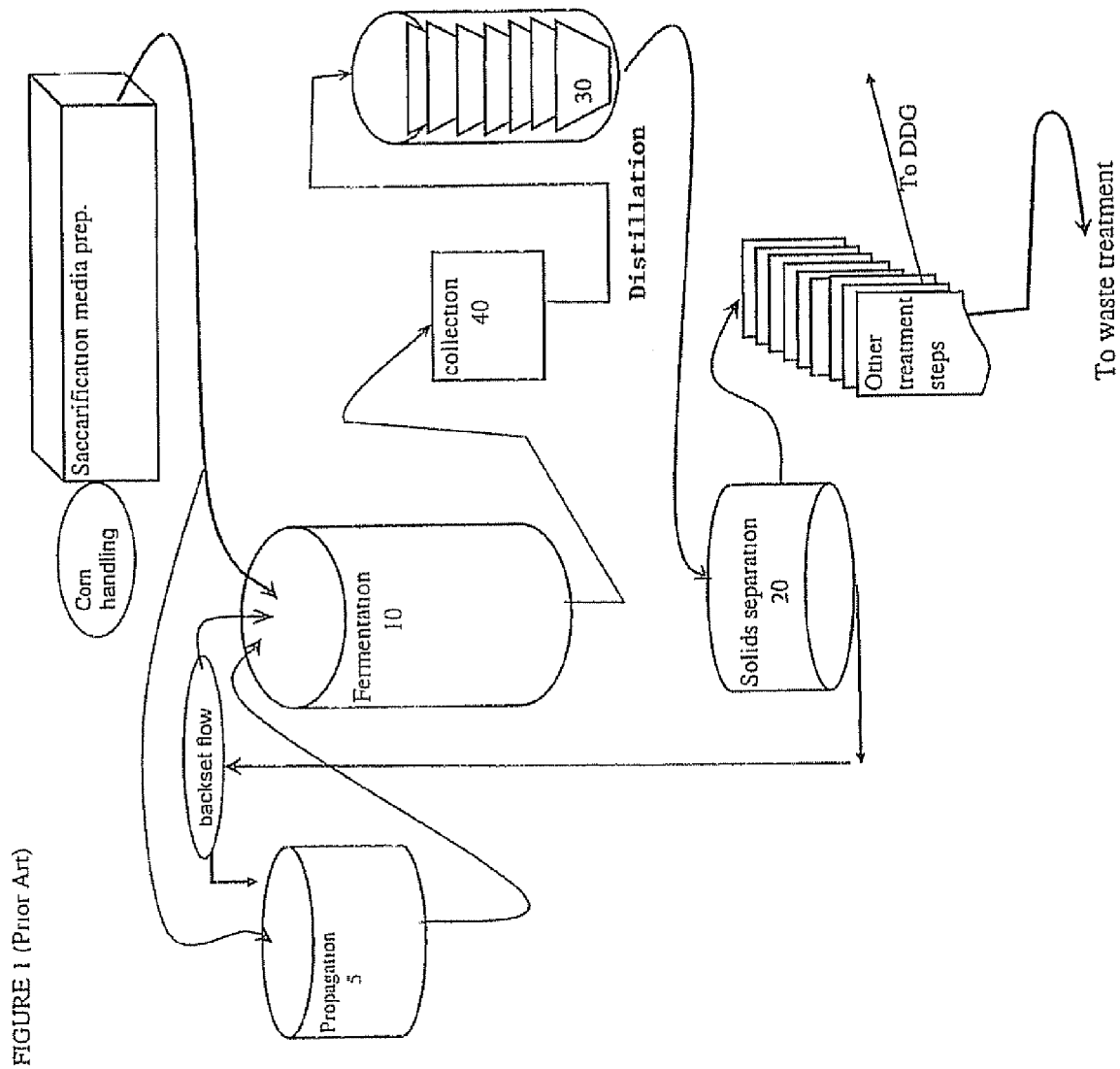
FIG. 1 illustrates a typical process for managing the media and byproduct streams in an ethanol fermentation plant.
Figure 2:
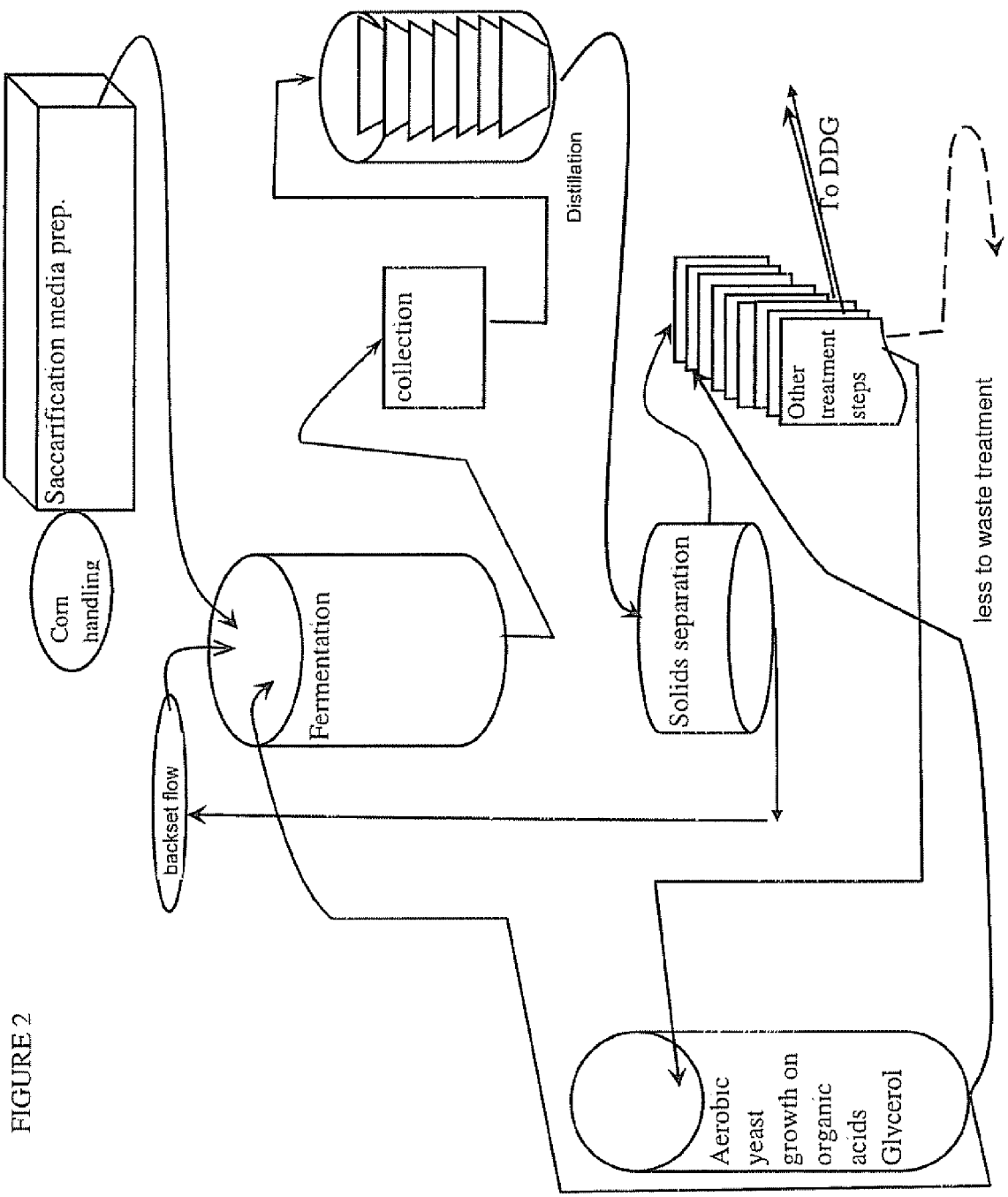
FIG. 2 illustrates one embodiment of an improvement provided by the present teaching.

Explanation of at least one embodiment of the invention may be made by reference to the figures. FIG. 2 illustrates one embodiment of an improvement provided by the present teaching. Instead of directing a large portion of the recycled concentrated organics to waste water and to low grade animal feed (such as DDGs), the concentrated OAGs ("cOAGs") are used to provide the primary carbon source for a second fermentation in aerobic fermentor 5A. In the absence of added dextrose or other sugars, the organic acids and glycerol are consumed by the yeast during aerobic fermentation.

The concentration of the OAGs added to the first aerobic fermentation may vary depending on their source; for example, they may vary depending on the originating facility. Nitrogen sources are usually present in the recycled streams in some amount but may have to be added to the first fermentation if the carbon to nitrogen ratio is too high. Other nutrients were found to be in adequate amounts in the recycle streams that were tested, but use of streams from other sources may require addition of one or more nutrients.

The water content typically varies from less than 80%, if a recycle stream with high solids content is desired, or between 80% and 99% if a recycle stream with a lower solids content is desired. Solids tolerance of a system may depend on a number of factors, including the source of the recycle stream and the effect on osmotic pressure in the fermentor.

The OAG fermentation is aerated. The rate of utilization of OAGs may be limited by oxygen transfer rates in the OAG fermentation. This may be beneficial, for instance, if a slower fermentation is desired, for example to maintain a lower level of heat emissions from the fermentation.

The yeast-containing biomass made in the aerobic fermentor 5A may be used either as an inoculum to initiate further anaerobic fermentation into ethanol in anaerobic fermentor 10. It may also be used directly as a higher quality animal feed, for example, in the form of DDGs.

No particular concentration of cOAGs is required. Typically the two are proportional, and lower cOAG concentration will lead to a lower yeast yield. Typical compositions of organic acids and glycerol in the backset and as a concentrate are presented in Table 1. Of course, those numbers may vary depending on the nature of the fermentation and concentration.

TABLE 1

|  | Backset Amount | Concentrate Amount |
| --- | --- | --- |
| Acetic Acid | 400-2500 mg/L | 1500-7000 mg/L |
| Lactic Acid | 800-4000 mg/L | 4000-15,000 mg/L |
| Glycerol | 5-20 g/L | 20-50 g/L |

In a typical continuous practice, the amount of cOAGs fed into aerobic fermentor 5A is calibrated so that essentially all of the organic acids and about 25-75% of the glycerol are consumed by the yeast and converted into biomass. By "essentially all," it is meant that greater than 95% of the organic acids fed into the fermentor are consumed in a batch fermentation. Because the aerobic fermentation first consumes the organic acids, calibration of the fermentation to consume less than essentially all of the organic acids will greatly reduce the amount of glycerol that is consumed. In a preferred embodiment, essentially all of the organic acids and about 15% to 45% of the glycerol are consumed.

One way that the rate of consumption of OAGs may be adjusted is by adjusting the pH of the fermentation. In a typical fermentation, the pH is maintained at 4.2 to 4.8, with the addition of ammonia or an ammonium salt. In a fermentation of one embodiment of the invention, the pH is maintained between 5-0 and 6.5, typically about 5.5, with the addition of a base. This base may be, for example, ammonia or sodium hydroxide. Ammonia is typically used, because it is also able to provide a nitrogen source for the growth of the yeast.

As organic acids are consumed the pH of the broth in the fermentor will rise. The higher pH levels are the result of this phenomenon. If needed, ammonium salts used as nitrogen source will mitigate that problem. As the nitrogen is utilized pH will be reduced.

Although other additives required for biomass propagation may be included in the aerobic fermentation, typically none are necessary when the anaerobic fermentation yielding the OAG stream is part of a dry-grind ethanol production process. Where the OAG stream is a product of a wet-grind fermentation, addition of some micronutrients may be beneficial or even necessary.

The rate of draw from aerobic fermentor 5A to innoucla or DDGs can be balanced with the rate of feed of cOAGs and consumption to form biomass so that in practice, the fermentation media in aerobic fermentor 5A contains a steady state level of glycerol and very low levels of organic acids while continually producing biomass. Low levels of glycerol can be attained if a second reactor in a row is be added. In such a reactor glycerol will preferably be used as the sole carbon source.

Although the examples and description presented herein use yeast as an exemplary organism capable of utilizing both aerobic and anaerobic fermentation, other facultative organisms that are able to use both five-carbon and six-carbon substrates as fuel may benefit from the invention. Embodiments of the invention provide methods to use the carbon-containing by-product of anaerobic fermentation as a substrate for aerobic fermentation, based on the use of different fuels for the different kinds of fermentation. In addition to yeasts, organisms that may take advantage of these methods may include, for example, facultative anaerobes such as members of the genera *Proteus, Serratia, Erwinia Vibrio, Aeromonas*, and *Photobacterium*.

Figure 3:
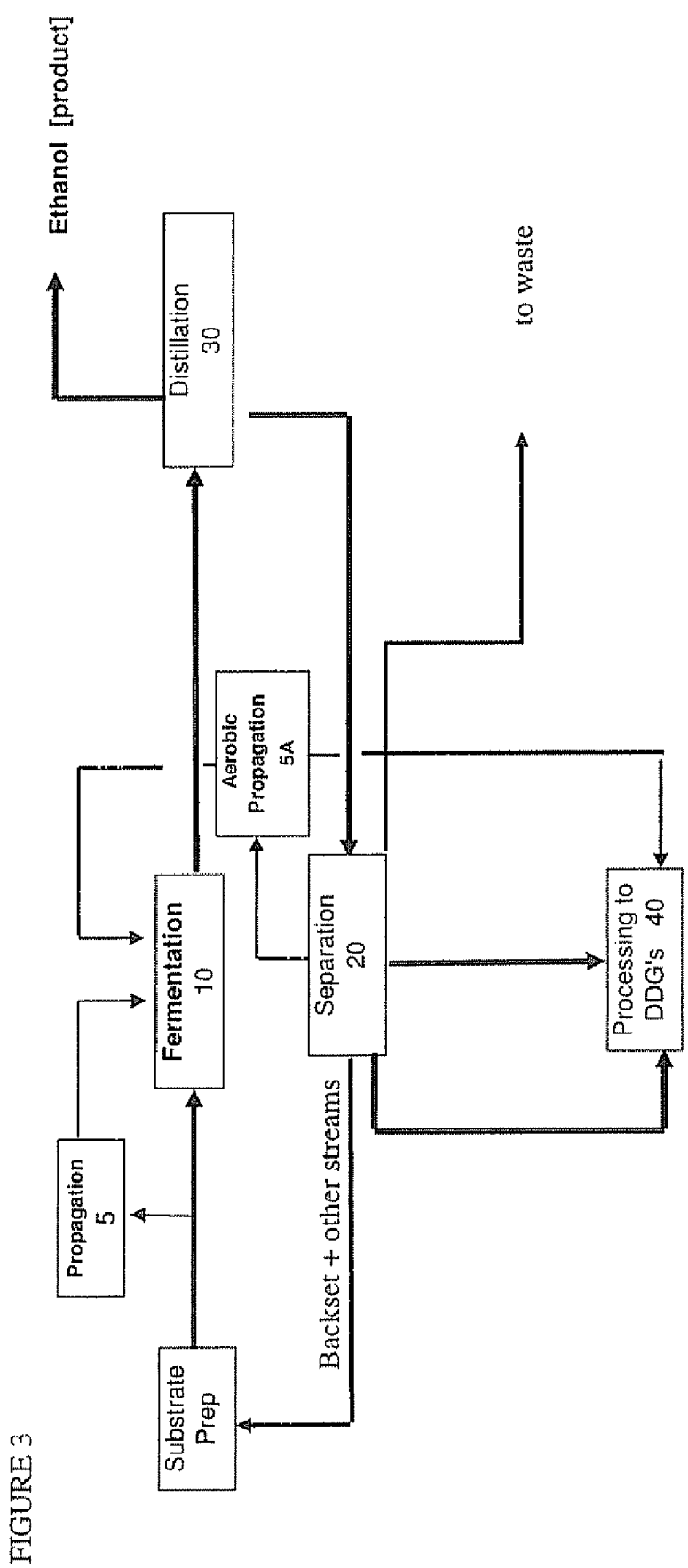
FIG. 3 illustrates a comparison of a typical process of FIG. 1 with an improved process provided in this disclosure. The typical process step is shown in dotted lines.

The present teaching offers several advantages over the prior art processes. Of course, these advantages should not be construed as requirements or as limitations unless they are explicitly included in the claims. First, it reduces the amounts of OAGs and other components that must be disposed of as aqueous waste. Second, it captures value from the otherwise negative value organic acids and glycerol byproducts of ethanol fermentation by converting them into higher value DDGs or more yeast for further ethanol production in the form of a non-carbohydrate based inoculum. Last, it reduces the inhibitory effects incident to adding too much OAG backset into the original second fermentation, while capturing and reusing some of the water in the system. An embodiment of the invention is compared to a prior art process in FIG. 3. Typically the fraction of the recycled water going to the inoculation train is small relative the portion that goes to the second fermentation.

Example 1

Example 1 reports batch fermentor growth of *Saccharomyces cerevisiae* on organic acids and glycerol obtained as a byproduct from the evaporation of the backset from a dry grind ethanol production facility. A batch yeast propagation was conducted in two 3.5 L fermentors. The OAG was concentrated to between 5 to 10 times the original OAG concentration.

The pH of the culture was adjusted to 4.4 using sodium hydroxide. Nitrogen was also added to the mixture as ammonium salts until the concentration of nitrogen (as ammonia) was 2.5 g/L. The inoculation ratio was 1% v/v.

Figure 4:
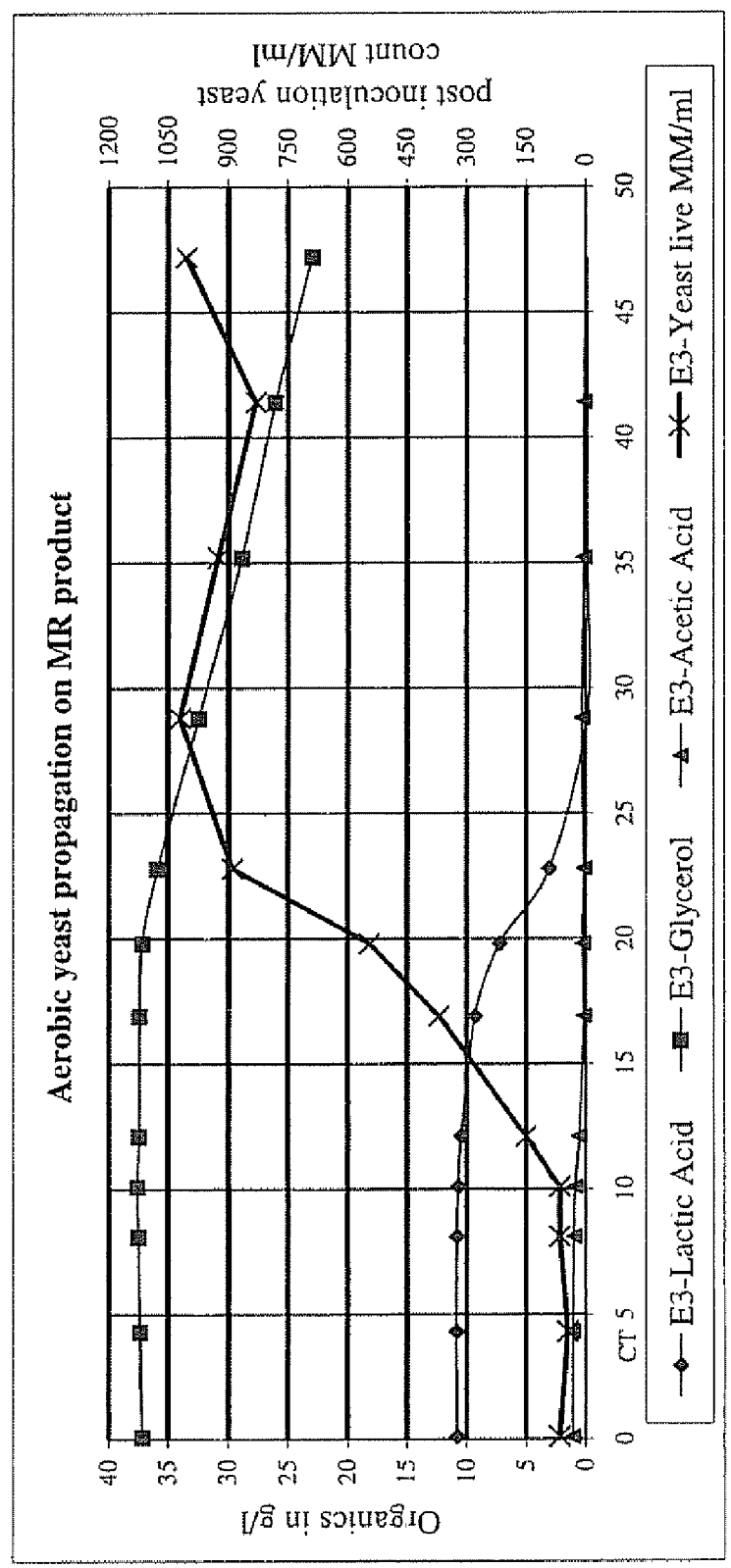
FIG. 4 shows the results of an aerobic batch yeast propagation according to one embodiment, as reported in Example 1.

Results are shown in FIG. 4. Organic acids are the preferred metabolite of the yeast. The preference for glycerol was secondary. Organic acid depletion was indicated by a significant increase in dissolved oxygen concentration, which is not shown in the graph.

The culture reached about $9 \times 10^8$ cells/ml within 24 hours and used 15-17 g/L of the carbon sources during that time. Both lactic acid and acetic acid were removed below the detection threshold, and about 40% of the glycerol was utilized mostly between the time the organic acids were depleted and the end of the run. Initial culture growth may be increased by using ammonia both as the nitrogen source and for pH adjustment.

Example 2

Example 2 reports growth of *Saccharomyces cerevisiae* on organic acids and glycerol obtained as a byproduct from the evaporation of the backset from a dry grind ethanol production facility. Fermentation was initially conducted as a batch process, then moved to a continuous fermentor after a yeast mass of over $5 \times 10^8$ deemed sufficient was reached.

Figure 5:
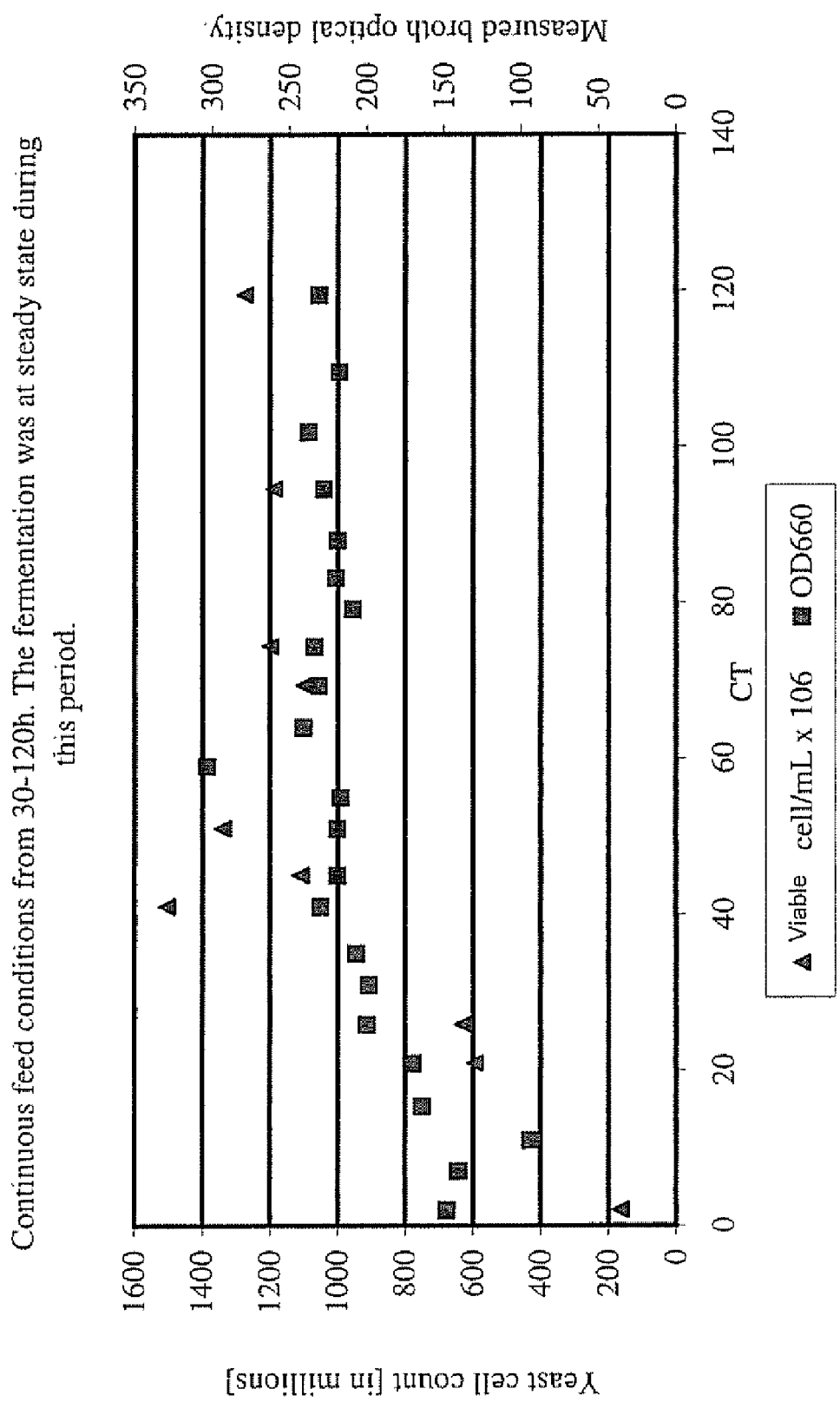
FIG. 5 shows viable cell count (measured in number of cells and by optical density) for the continuous fermentation reported in Example 2.

After being moved to a continuous fermentation mode the fermentation rapidly reached steady state conditions at 5 to 6 hour retention time. As shown in FIG. 5, culture density as expressed by optical density (OD at 660 nm) or by viable yeast cell count remained steady for the duration of the continuous feed/drop phase, which lasted 90 hours. During this period about 16 fermentor volumes were generated. Average yeast concentration during the continuous phase was $1.2 \times 10^9$ cells/mL.

Figure 6:
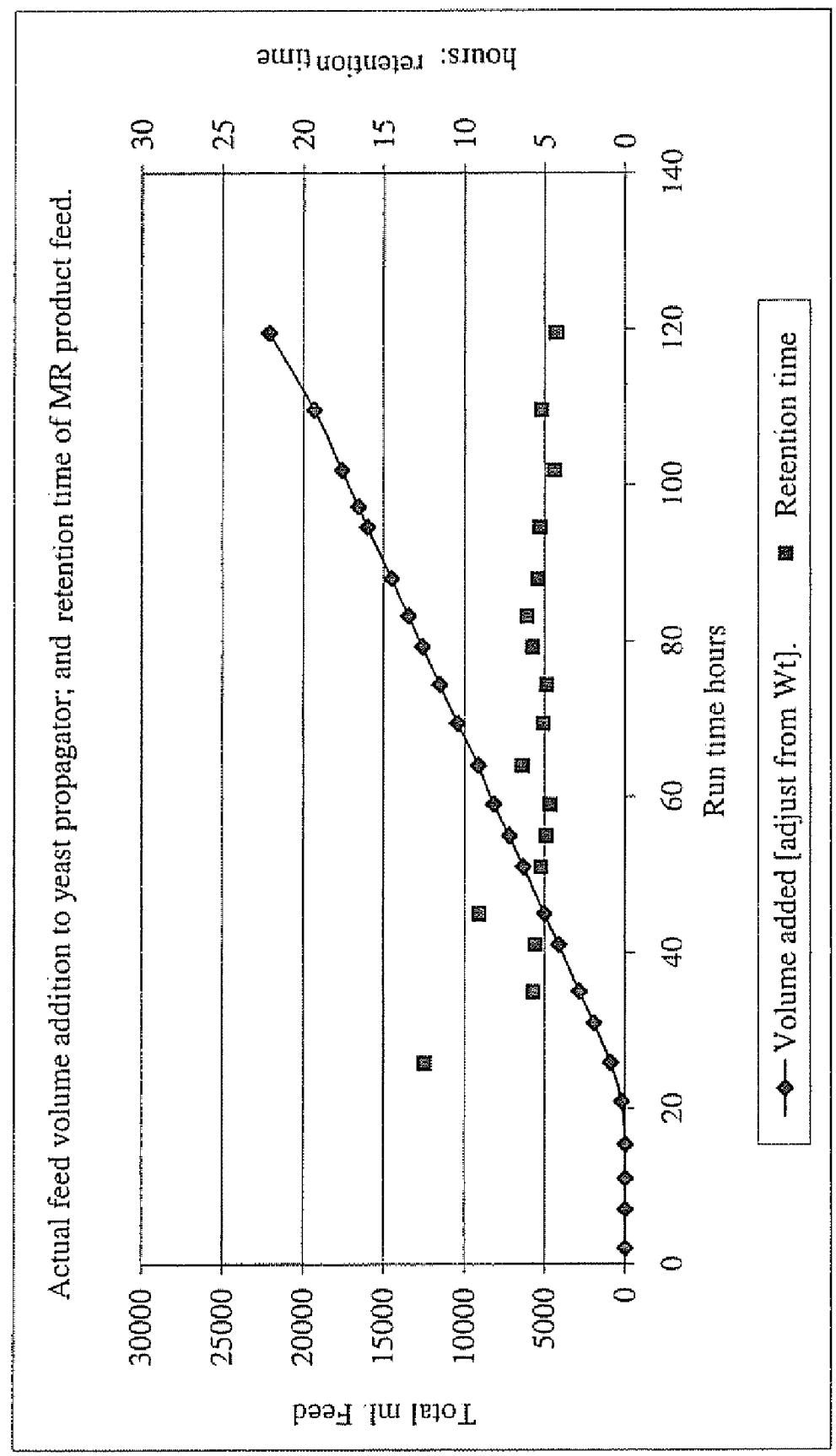
FIG. 6 shows feed addition and retention time for the continuous fermentation in Example 2.

FIG. 6 shows the consistency of the fermentation described in this example. The small variances in retention time are mostly the result of different assessments of running fermentor volume. Like Example 1, propagation of yeast in this example requires the carbon source and an added nitrogen source. Adjustment of pH to an optimum growth level (about 4.0 to 5.5) is also desirable.

Example 3

Figure 7:
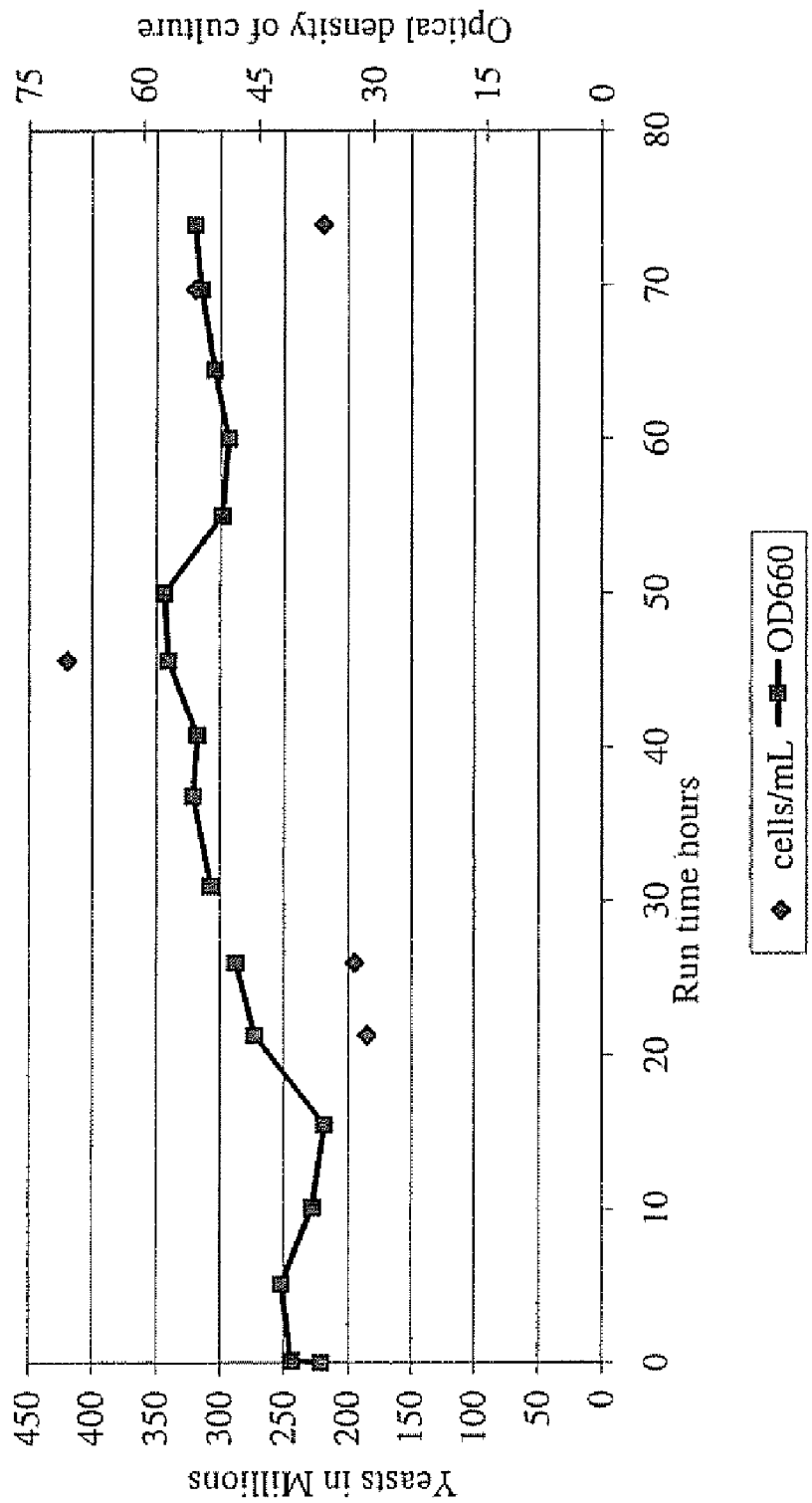
FIG. 7 shows viable cell count for yeast growth on unconcentrated OAG as reported in Example 3.

Example 3 shows yeast growth on organic acids according to another embodiment of the invention. Conditions were the same as Example 2, but the organic acids are not concentrated. The results of this Example are shown in FIG. 7. Growth was limited by low substrate concentration, as indicated by the low optical density and yeast concentration when compared to the results of Example 2.

Patents, patent applications, publications, scientific articles, books, and other documents and materials referenced or mentioned herein are indicative of the levels of skill of those skilled in the art to which the inventions pertain, as of the date each publication was written, and all are incorporated by reference as if fully rewritten herein. Inclusion of a document in this specification is not an admission that the document represents prior invention or is prior art for any purpose.

The terms and expressions employed herein have been used as terms of description and not of limitation, and there is no intention in the use of such terms and expressions, or any portions thereof, to exclude any equivalents now know or later developed, whether or not such equivalents are set forth or shown or described herein or whether or not such equivalents are viewed as predictable, but it is recognized that various modifications are within the scope of the invention claimed, whether or not those claims issued with or without alteration or amendment for any reason. Thus, it shall be understood that, although the present invention has been specifically disclosed by preferred embodiments and optional features, modifications and variations of the inventions embodied therein or herein disclosed can be resorted to by those skilled in the art, and such modifications and variations are considered to be within the scope of the inventions disclosed and claimed herein.

Specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. Where examples are given, the description shall be construed to include but not to be limited to only those examples.

It will be readily apparent to one skilled in the art that varying substitutions and modifications may be made to the invention disclosed herein without departing from the scope and spirit of the invention, and from the description of the inventions, including those illustratively set forth herein, it is manifest that various modifications and equivalents can be used to implement the concepts of the present invention without departing from its scope. A person of ordinary skill in the art will recognize that changes can be made in form and detail without departing from the spirit and the scope of the invention, the described embodiments are to be considered in all respects as illustrative and not restrictive. Thus, for example, additional embodiments are within the scope of the invention and within the following claims.

I claim:

1. A method for making ethanol by fermentation, comprising:
   (a) growing an ethanol producing microorganism under first growth conditions in a first medium consisting of a backset comprising a carbon source having at least one member selected from the group consisting of organic acid and glycerol to form an inoculation broth, said backset being obtained by growing the microorganism in a second medium to produce ethanol by fermentation and distillation of the second medium to remove the ethanol in accordance with steps (b) and (c) below, said second medium comprising a carbon source comprising at least one member of the group consisting of a sugar or polysaccharide of at least 5 carbon atoms;
   (b) inoculating the second medium with the inoculation broth obtained from step (a) and growing the microorganism in the second medium under second conditions suitable for producing ethanol:
   (c) distilling the ethanol and removing said microorganisms from the second medium to obtain the backset; and
   (d) repeating step (a) using the backset obtained from step (c).

2. The method of claim 1, wherein said ethanol producing microorganism is *Saccharomyces cerevisiae*, said first medium consisting essentially of water, acetic acid, lactic acid, and glycerol, and said second medium consists essentially of water and dextrose.

3. The method of claim 2, including conducting the growth step of step (a) in a continuous fermentor, wherein said yeast concentration is at least $1.5 \times 10^9$ cells/ml and the growth rate is at least $3 \times 10^8$ g/L/hour.

4. The method of claim 1, wherein said fermentation is selected from the group consisting of a continuous fermentation and a batch fermentation.

5. A method for making ethanol by fermentation, comprising
   (a) growing an ethanol producing microorganism under aerobic conditions in a first medium consisting of a backset comprising a carbon source having at least one member selected from of the group consisting of organic acid and glycerol to form an inoculation broth said backset being obtained as a by-product of growing the microorganism under anaerobic conditions to produce ethanol by fermentation and distillation of the second medium to remove the ethanol;
(b) combining the inoculation broth with a second medium comprising a carbon source comprising at least one member of the group consisting of a sugar and a polysaccharide of at least 5 carbon atoms;
(c) growing the microorganism under anaerobic conditions to produce ethanol and a byproduct comprising at least one member of the group consisting of organic acid and glycerol;
(d) distilling the second medium to remove ethanol to form a backset medium comprising the by product; and
(e) repeating step s (a) through (d) using the backset medium obtained from step (d) as the backset of step (a).

6. The method of claim 5, wherein said microorganism is *Saccharomyces cerevisiae*, said first medium consists essentially of lactic acid, acetic acid, glycerol, and water, and said second medium consists essentially of water, and dextrose.

7. A method for making a primary product by fermentation, comprising
(a) growing a microorganism culture that produces the primary product under first fermentation conditions in a first medium to form an inoculation broth, the first medium comprising a first nutrient source consisting of a by-product of fermentation of the same microorganism culture grown under second fermentation conditions selected to produce the primary product according to steps (b)-(d) below;
(b) inoculating a second fermentation medium with the inoculation broth obtained from step (a) and growing the microorganism culture under the second fermentation conditions in the second medium wherein the second medium comprises a second nutrient source different from the first nutrient source and the second fermentation conditions are selected to produce the primary product and the by-product containing the primary nutrient source referenced in step (a);
(c) separating the by-product containing the primary nutrient source and the microorganisms from the primary product in the second medium to obtain a by-product stream containing the primary nutrient source; and
(d) repeating step (a) by providing the by-product stream of step (c) to grow the microorganism culture to form the inoculation broth according to step (a).

8. The method of claim 7, comprising the step of concentrating said by-product stream prior to growing said microorganism culture in said first medium.

9. The method of claim 8, wherein said first fermentation conditions are aerobic, said second fermentation conditions are anaerobic, said first medium consists essentially of lactic acid, acetic acid, water, and glycerol, said second medium consists essentially of water and dextrose, said primary product is ethanol, and said microorganism culture is a *Saccharomyces cerevisiae* culture.

10. The method of claim 7, wherein said first fermentation conditions are aerobic and said second fermentation conditions are anaerobic.

11. The method of claim 7, wherein said first medium consists essentially of lactic acid, acetic acid, water, and glycerol.

12. The method of claim 7, wherein said second medium consists essentially of water and dextrose.

13. The method of claim 7, wherein said primary product is ethanol and said microorganism culture is a yeast culture.

14. The method of claim 7, wherein said microorganism culture is selected from the group consisting of a *Saccharomyces cerevisiae* culture, a *Corynebacterium* culture, a *Staphylococcus* culture, and a *Listeria* culture.

15. The method of claim 7, wherein said microorganism culture is a *Saccharomyces cerevisiae* culture.

\* \* \* \* \*